US008870895B2

(12) United States Patent
Bilitz

(10) Patent No.: US 8,870,895 B2
(45) Date of Patent: *Oct. 28, 2014

(54) MEDICAL RETRIEVAL DEVICE WITH INDEPENDENT ROTATIONAL MEANS

(75) Inventor: Mark R. Bilitz, Plymouth, MN (US)

(73) Assignee: Annex Medical, Inc., Eden Prairie, MN (US)

( * ) Notice: Subject to any disclaimer, the term of this patent is extended or adjusted under 35 U.S.C. 154(b) by 34 days.

This patent is subject to a terminal disclaimer.

(21) Appl. No.: 13/236,031

(22) Filed: Sep. 19, 2011

(65) Prior Publication Data
US 2012/0095477 A1 Apr. 19, 2012

Related U.S. Application Data

(63) Continuation of application No. 10/190,218, filed on Jul. 5, 2002, now Pat. No. 8,021,372.

(60) Provisional application No. 60/303,114, filed on Jul. 5, 2001.

(51) Int. Cl.
*A61B 17/22* (2006.01)
*A61B 17/221* (2006.01)
*A61B 17/29* (2006.01)

(52) U.S. Cl.
CPC ....... *A61B 17/221* (2013.01); *A61B 2017/2212* (2013.01); *A61B 17/2909* (2013.01); *A61B 2017/2929* (2013.01)
USPC .......................... 606/127; 606/113; 606/114

(58) Field of Classification Search
USPC .......................... 606/110, 113, 114, 127, 128
See application file for complete search history.

(56) References Cited

U.S. PATENT DOCUMENTS

| | | | |
|---|---|---|---|
| 651,395 A | 6/1900 | Stapp | |
| 1,677,671 A | 7/1928 | Councill | |
| 2,918,919 A | 12/1959 | Wallace | |
| 2,943,626 A | 7/1960 | Dormia | |
| 3,008,467 A | 11/1961 | Morris | |
| 3,791,387 A | 2/1974 | Itoh | |
| 3,828,790 A | 8/1974 | Curtiss et al. | |
| 3,903,892 A | 9/1975 | Komiya | |
| 3,955,578 A * | 5/1976 | Chamness et al. | 606/47 |
| 4,046,149 A | 9/1977 | Komiya | |

(Continued)

OTHER PUBLICATIONS

Application and file history for U.S. Appl. No. 11/094,894, filed Mar. 31, 2005. Inventors: Lind et al.

(Continued)

*Primary Examiner* — Ryan Severson
(74) *Attorney, Agent, or Firm* — Patterson Thuente Pedersen, P.A.

(57) ABSTRACT

A medical retrieval device used to remove objects such as urinary and biliary calculi from the body comprising a handle assembly with an independent rotational means, a sheath, and an object entrapping assembly. In preferred embodiments, the handle assembly comprises a longitudinally stationary base portion with a handle base and a rotating means and a thumb slide actuation means located between the distal and proximal ends of the handle base portion. Actuation of the thumb slide relative to the handle base causes the object entrapping assembly to be actuated between the open and closed positions. Rotation of the rotating means relative to the handle base causes precise rotation of the object entrapping assembly. The thumb slide actuation means and rotating means are separate and independent of each other, preventing inadvertent adjustment of the degree of actuation during rotation and preventing inadvertent adjustment of rotational position during actuation.

3 Claims, 6 Drawing Sheets

(56) References Cited

U.S. PATENT DOCUMENTS

| | | | |
|---|---|---|---|
| 4,046,150 A | 9/1977 | Schwartz et al. | |
| 4,198,960 A | 4/1980 | Utsugi | |
| 4,299,225 A | 11/1981 | Glassman | |
| 4,347,846 A | 9/1982 | Dormia | |
| 4,590,938 A | 5/1986 | Segura et al. | |
| 4,611,594 A | 9/1986 | Grayhack et al. | |
| 4,612,931 A | 9/1986 | Dormia | |
| 4,625,726 A | 12/1986 | Duthoy | |
| 4,633,871 A | 1/1987 | Shinozuka | |
| 4,655,219 A | 4/1987 | Petruzzi | |
| 4,790,812 A | 12/1988 | Hawkins, Jr. et al. | |
| 4,807,626 A | 2/1989 | McGirr | |
| 4,815,476 A | 3/1989 | Clossick | |
| 4,927,426 A | 5/1990 | Dretler | |
| 4,994,079 A | 2/1991 | Genese et al. | |
| 5,057,114 A | 10/1991 | Wittich et al. | |
| 5,064,428 A | 11/1991 | Cope et al. | |
| 5,066,295 A * | 11/1991 | Kozak et al. | 606/47 |
| 5,146,928 A | 9/1992 | Esser | |
| 5,176,688 A | 1/1993 | Narayan et al. | |
| 5,201,741 A | 4/1993 | Dulebohn | |
| 5,330,482 A | 7/1994 | Gibbs et al. | |
| 5,376,094 A | 12/1994 | Kline | |
| 5,484,384 A | 1/1996 | Fearnot | |
| 5,496,330 A * | 3/1996 | Bates et al. | 606/127 |
| 5,499,981 A | 3/1996 | Kordis | |
| 5,573,530 A | 11/1996 | Fleury et al. | |
| 5,718,714 A | 2/1998 | Livneh | |
| 5,722,423 A | 3/1998 | Lind et al. | |
| 5,788,710 A * | 8/1998 | Bates et al. | 606/127 |
| 5,792,145 A | 8/1998 | Bates et al. | |
| 5,817,104 A | 10/1998 | Bilitz et al. | |
| 5,820,630 A | 10/1998 | Lind | |
| 5,891,017 A | 4/1999 | Swindle et al. | |
| 5,944,728 A | 8/1999 | Bates | |
| 5,957,932 A * | 9/1999 | Bates et al. | 606/127 |
| 5,989,266 A | 11/1999 | Foster | |
| 6,015,415 A | 1/2000 | Avellanet | |
| 6,053,934 A | 4/2000 | Andrews et al. | |
| 6,090,129 A | 7/2000 | Ouchi | |
| 6,093,196 A * | 7/2000 | Okada | 606/127 |
| 6,096,053 A | 8/2000 | Bates | |
| 6,159,220 A | 12/2000 | Gobron et al. | |
| 6,168,603 B1 * | 1/2001 | Leslie et al. | 606/114 |
| 6,183,482 B1 * | 2/2001 | Bates et al. | 606/127 |
| 6,190,394 B1 | 2/2001 | Lind et al. | |
| 6,203,552 B1 | 3/2001 | Bagley et al. | |
| 6,224,612 B1 | 5/2001 | Bates et al. | |
| 6,235,026 B1 | 5/2001 | Smith | |
| 6,258,101 B1 | 7/2001 | Blake, III | |
| 6,280,451 B1 | 8/2001 | Bates et al. | |
| 6,319,262 B1 * | 11/2001 | Bates et al. | 606/127 |
| 6,325,807 B1 | 12/2001 | Que | |
| 6,348,056 B1 | 2/2002 | Bates et al. | |
| 6,350,266 B1 | 2/2002 | White et al. | |
| 6,352,539 B1 | 3/2002 | Avellanet | |
| D457,955 S | 5/2002 | Bilitz | |
| 6,398,791 B1 | 6/2002 | Que et al. | |
| 6,419,679 B1 * | 7/2002 | Dhindsa | 606/127 |
| 6,494,885 B1 * | 12/2002 | Dhindsa | 606/127 |
| 6,500,182 B2 | 12/2002 | Foster | |
| 6,527,781 B2 | 3/2003 | Bates et al. | |
| 6,551,327 B1 * | 4/2003 | Dhindsa | 606/127 |
| 6,575,970 B2 | 6/2003 | Quick | |
| 6,626,915 B2 | 9/2003 | Leveillee | |
| 6,676,668 B2 | 1/2004 | Mercereau et al. | |
| 6,695,834 B2 | 2/2004 | Gellman et al. | |
| 6,740,030 B2 | 5/2004 | Martone et al. | |
| 6,743,237 B2 * | 6/2004 | Dhindsa | 606/127 |
| 6,752,811 B2 | 6/2004 | Chu et al. | |
| 7,101,379 B2 | 9/2006 | Gregory, Jr. et al. | |
| 8,021,372 B2 | 9/2011 | Bilitz | |
| 8,523,879 B1 | 9/2013 | Lind et al. | |
| 2001/0001315 A1 | 5/2001 | Bates et al. | |
| 2002/0026202 A1 | 2/2002 | Honey et al. | |
| 2002/0068954 A1 | 6/2002 | Foster | |
| 2002/0133170 A1 | 9/2002 | Tsuruta | |
| 2002/0133171 A1 | 9/2002 | Que et al. | |
| 2003/0009176 A1 | 1/2003 | Bilitz | |
| 2003/0023247 A1 | 1/2003 | Lind et al. | |
| 2003/0055401 A1 | 3/2003 | Larson et al. | |
| 2003/0078593 A1 | 4/2003 | Bates et al. | |
| 2003/0088254 A1 | 5/2003 | Gregory, Jr. et al. | |
| 2003/0105480 A1 | 6/2003 | Wiener et al. | |
| 2003/0120281 A1 | 6/2003 | Bates et al. | |
| 2003/0139750 A1 | 7/2003 | Shinozuka et al. | |
| 2003/0225419 A1 | 12/2003 | Lippitt et al. | |
| 2004/0122444 A1 | 6/2004 | Gerard | |
| 2004/0133213 A1 | 7/2004 | Bagley et al. | |
| 2004/0199048 A1 | 10/2004 | Clayman et al. | |
| 2004/0215212 A1 | 10/2004 | Teague et al. | |
| 2005/0125016 A1 | 6/2005 | Trerotola | |

OTHER PUBLICATIONS

Application and file history for U.S. Appl. No. 10/190,218, filed Jul. 5, 2002. Inventors: Bilitz et al.

Application and file history for U.S. Appl. No. 10/831,986, filed Apr. 26, 2004. Inventors: Dostal et al.

Application and File history for U.S. Appl. No. 12/821,792, filed Jun. 23, 2010. Inventors: Dostal et al.

Application and File history for U.S. Appl. No. 10/964,281, filed Oct. 13, 2004. Inventors: Lind et al.

* cited by examiner

MEDICAL RETRIEVAL DEVICE WITH INDEPENDENT ROTATIONAL MEANS

PRIORITY CLAIM

This application is a continuation of U.S. patent application Ser. No. 10/190,218, filed Jul. 5, 2002, now U.S. Pat. No. 8,021,372, which claims priority to U.S. Provisional Application Ser. No. 60/303,114, filed on Jul. 5, 2001, which are incorporated herein by reference.

BACKGROUND OF THE INVENTION

1. Field of Invention

This invention relates to medical retrieval devices for removing objects from a body, particularly calculi from the urinary and biliary systems.

2. Description of Prior Art

Medical instruments are currently in use which reduce the invasiveness and potential trauma previously associated with various medical procedures. One such procedure is the removal of objects, such as kidney stones and gallstones, from the body. Various surgical devices are available which allow objects to be removed from the body without requiring major surgery. One type of surgical device is a mechanical retrieval device. Typically, such instruments consist of 2 or more flexible elements that are joined at their proximal ends and may or may not be joined at their distal ends. The flexible elements are formed in the shape of a basket, cage, grasper, or other entrapping configuration. This basket is attached to a drive wire that passes through the lumen of a small diameter (typically 2.3 mm (7.0 Fr) or less) flexible sheath, which is usually greater than 50 cm in length. The proximal ends of the sheath and drive wire are attached to a multi-part handle, normally constructed of thermoplastic materials, which can typically be operated by the user with a single hand. By manipulating the handle, the drive wire can be pulled back relative to the sheath, collapsing the basket as it retracts into the sheath. In this closed position, the sheath can be passed through the working channel of an endoscope to the proximity of the object to be removed within the patient's body. The basket is expanded to the open position by manipulating the handle, which remains outside the endoscope and the patient's body. The device is then manipulated using the handle until the object becomes enclosed within the basket. This manipulation may include advancing, withdrawing and/or rotating the basket in order to get the object to pass between the flexible elements that comprise the basket. When the object has been successfully engaged within the basket, the endoscope and the retrieval device containing the object are then simultaneously removed from the body.

A number of designs for the handle of medical retrieval devices are in use. Typically, these handles consist of two main elements, a handle base and an actuation mechanism. The sheath is attached to one of these elements, and the drive wire is attached to the other. By moving the actuation mechanism relative to the handle base, the basket can be retracted into the sheath and extended from it. The handle design that appears to be preferred, based on actual current use and sales volumes, is of a thumb slide design. This design features a main handle base that remains stationary and a thumb slide actuator that slides along a portion of the handle body and has a thumb pad. This handle is held in one hand by wrapping the four fingers of the hand partially around the handle base. The thumb of the same hand is placed on the thumb pad. The device is actuated in one direction by moving the thumb pad away from the proximal end of the handle base, and in the other direction by moving the thumb pad toward the proximal end of the handle base. This type of handle can normally be held in such a way that the range of motion of the thumb required to fully actuate the device is located in a natural and comfortable area near the thumb's resting position. Since considerable skill and dexterity can be required of the user in order to retrieve an object, user comfort is of primary importance.

There are many variations of the thumb slide handle in use. However, these and other prior art handle designs do not have a mechanism for rotating the basket to facilitate capturing the object. Rotation can only be accomplished by rotating the entire handle. This method has a number of disadvantages. By rotating the entire handle, the user must accordingly rotate their hand. Since the hand would initially be placed in a natural position, the position of the hand after rotation would not necessarily be comfortable for further manipulation of the handle. Again, user comfort is significant due to the considerable skill and dexterity needed to successfully complete a stone retrieval procedure. Additionally, since the entire handle must be rotated in order to rotate the basket, the sheath must rotate as well as the drive wire. This is a disadvantage because the friction between the sheath and the endoscope's working channel can prevent a smooth 1:1 torque ratio between the handle and the basket. This is particularly relevant when the endoscope is flexible and is in an articulated position. Lack of precise rotational control can increase the difficulty of engaging the object in the basket, thereby lengthening the procedure.

Certain handle designs have been used which allow rotation of the basket without rotating the entire handle and thus the sheath as well. U.S. Pat. No. 4,046,150 (1977) to Schwartz et al. discloses a retrieval basket with such a handle. This handle has a first member that is attached to the sheath. A second member, which is attached to the drive wire, is located at the proximal end of the first member. The device is actuated by sliding the second member into and out of the first member, which is held stationary. The basket is rotated relative to the sheath by rotating the second member relative to the first member. However, this handle is not of the preferred thumb slide style, and requires the use of two hands to actuate. Also, the actuational and rotational controls are not independent of each other.

U.S. Pat. No. 5,957,932 (1999) to Bates et al. discloses a retrieval basket with yet another type of handle. This handle is of a pistol grip style, with a control knob located at the proximal end of the handle. The sheath is attached to the main body of the handle, and the drive wire is attached to the control knob. The device is actuated by pulling the control knob out from the main body of the handle and pushing it in. The control knob can also be rotated to rotate the basket. When the trigger portion of the handle is squeezed, mechanical advantage is applied to the actuation of the device. This design has several disadvantages. It requires two hands for normal actuation. And since the control knob is used for both actuation and rotation of the basket, the actuation and rotation are not independent of each other. It also uses a larger number of parts than other handle designs and is therefore is more complex and more expensive to manufacture. The above patents to Schwartz and Bates are incorporated herein by reference.

Another type of prior art handle, which is not referenced in any patents, is shown in FIGS. 7 and 8. A handle assembly 190 consists of a stationary portion or handle base 110 and a thumb slide 130 with a thumb pad 131. Handle base 110 has a distal end 181, a proximal end 182, and a length 180. Thumb slide 130 fits partially within handle base 110 and extends out from distal end 181, with thumb pad 131 remaining beyond distal end 181. A hollow tube or sheath 150 has a working length 186 and is attached to thumb slide 130. A drive wire (not shown) passes through the lumen of sheath 150 attaches at the proximal end to handle base 110 and at the distal end to a basket 160. To operate this device, handle base 110 is held in one hand with the four fingers of the hand. The thumb of the same hand is placed on thumb pad 131. When the thumb is extended away from the hand, thumb slide 130 slides out from distal end 181 of handle base 110. This results in the device being in the closed position, as shown in FIG. 7. When the thumb is pulled back toward the hand, thumb pad 131 slides toward distal end 181 of handle base 110. This results in sheath 150 being pulled back to expose basket 160. When thumb pad 131 is pulled back completely to handle base 110, the device is in the open position, as shown in FIG. 8. To rotate basket 160, handle base 110 is rotated relative to thumb slide 130. This design has the disadvantage that the actuation mechanism and the rotation mechanism are not independent. Both actuation and rotation are achieved by movement of the thumb slide and the handle base relative to each other. This design also has the disadvantage that the thumb pad is located beyond the distal end of the stationary handle base. This is a disadvantage because manipulation of the thumb slide is done with the user's thumb extended away from the hand in a somewhat awkward position, which results in less than ideal tactile control over the actuation of the device.

The prior art handle designs that do allow rotation of the basket without rotating the entire handle have the disadvantage that the rotation mechanism and actuation mechanism are not independent. As a result, while the basket is being rotated, it may be inadvertently and undesirably expanded or retracted, or while it is being expanded or retracted, it may be inadvertently and undesirably rotated. The retrieval of an object from within a patient's body using an endoscope and a retrieval device is a precise and delicate procedure that requires considerable user skill and dexterity. Since the user's control of the basket is limited by the handle of the device, it is desirable that the handle allows precise and independent control of both the actuation and rotation of the basket, and is comfortable to use.

SUMMARY OF THE INVENTION

A medical retrieval device used for extracting objects such as urinary and biliary calculi from the body comprising a handle assembly with an independent rotational means, a sheath, and an object entrapping assembly. In preferred embodiments, the handle assembly comprises a longitudinally stationary base portion and a thumb slide actuation means. The longitudinally stationary portion comprises a handle base and a rotating means. In a preferred embodiment, a portion of the thumb slide actuation means is located between the distal and proximal ends of the handle base portion during the complete actuation cycle. Actuation of the thumb slide relative to the handle base causes the object entrapping assembly to be actuated between the open and closed positions. Rotation of the rotating means relative to the handle base causes precise rotation of the object entrapping assembly. The thumb slide actuation means and rotating means are separate and independent of each other, preventing inadvertent adjustment of the degree of actuation during rotation and preventing inadvertent adjustment of rotational position during actuation.

An object and advantage of preferred embodiments of the invention is to provide a medical retrieval device with a mechanism for precisely rotating the basket that is independent of the actuation mechanism.

An object and advantage of preferred embodiments of the invention is to provide a medical retrieval device with a mechanism for rotating the basket that cannot inadvertently cause adjustment to the degree of actuation during rotation.

An object and advantage of preferred embodiments of the invention is to provide a medical retrieval device that permits rotation of the basket without requiring rotation of the entire handle assembly and/or the sheath.

An object and advantage of preferred embodiments of the invention is to provide a novel handle for a medical retrieval device that is of a thumb slide actuated type that is comfortable for the user to hold and operate.

An object and advantage of preferred embodiments is to provide a novel handle for a medical retrieval device that uses a minimal number of parts, reducing cost and simplifying assembly.

Further objects and advantages of preferred embodiments of the medical retrieval device described herein are that such preferred embodiments are safe, reliable, and easy to use. Still further objects and advantages will become apparent from a consideration of the ensuing description and drawings.

DETAILED DESCRIPTION OF THE DRAWINGS

Figure 1:
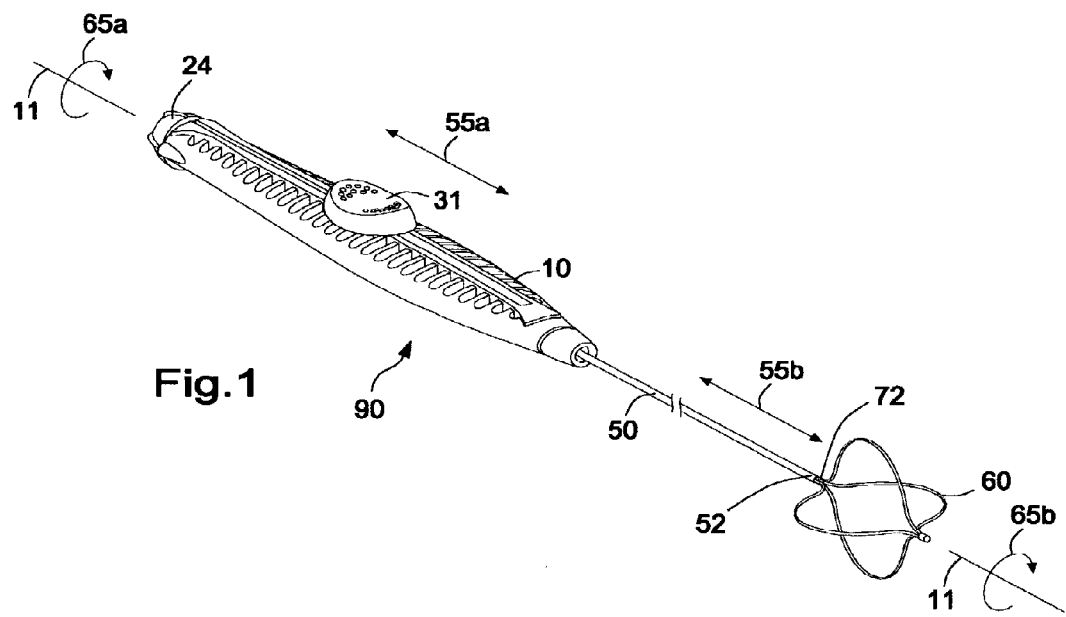
FIG. 1 is an isometric view of the preferred embodiment of the present invention.
Figure 2:
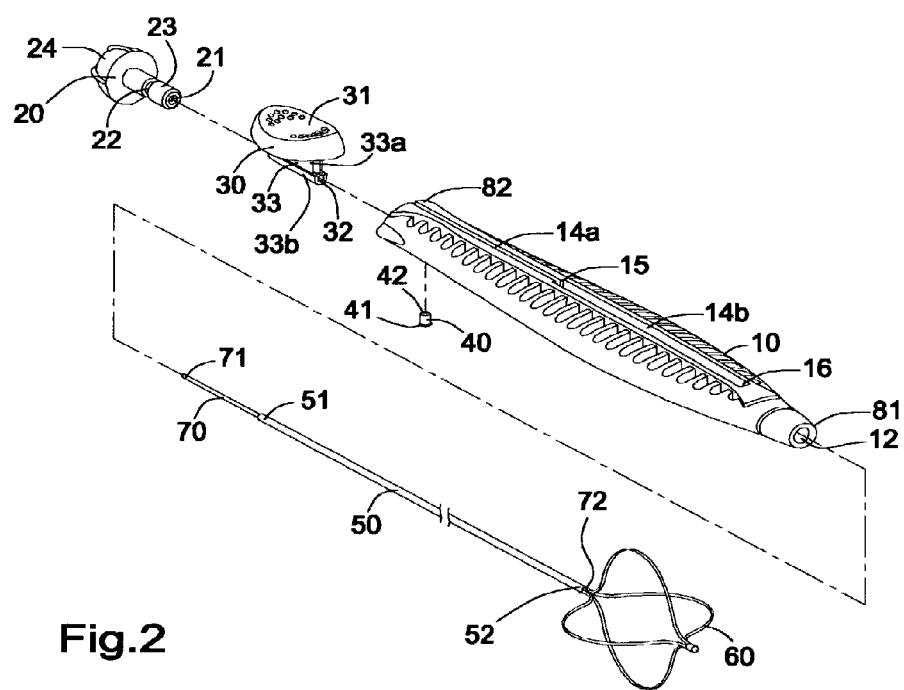
FIG. 2 is an exploded isometric view of FIG. 1.

FIGS. 1 to 6C show a preferred embodiment of the invention. A medical retrieval device has a handle assembly 90, which has a longitudinal axis 11. Handle assembly 90 is comprised of an elongate handle base 10, a rotation means or spinner 20, a sliding portion or thumb slide 30, and a pin 40, all of which are preferably constructed of thermoplastic materials. Handle base 10 has a proximal end 82, a distal end 81, and a length 80, which is between 5 and 20 cm. Handle base 10 is essentially hollow along longitudinal axis 11, with an internal bore and an opening 12 at distal end 81. A longitudinal slot having a narrow portion 14a and a wide portion 14b is located on the top surface of handle base 10. Wide portion 14b has a proximal end 15 and a distal end 16. Narrow portion 14a extends from proximal end 82 of handle base 10 to wide portion 14b. Distal end 16 of wide portion 14b is located proximal to distal end 81 of handle base 10.

Thumb slide 30 has a thumb pad 31 and a guide portion configured as a fin 33, which has an upper portion 33a and a lower portion 33b. The width of upper portion 33a of fin 33 is wider than the width of narrow portion of slot 14a and narrower than the width of wide portion of slot 14b. The width of lower portion 33b of fin 33 is wider than the width of wide portion of slot 14b. A through hole 32 passes through lower portion 33b of fin 33 longitudinally. Thumb slide 30 is located on handle base 10 with upper portion 33a of fin 33 located within wide portion of slot 14b and lower portion 33b of fin 33 located within the hollow portion of handle base 10 below wide portion 14b. With thumb slide 30 engaged with wide portion of slot 14b in this manner, thumb slide 30 can be readily moved so that fin 33 is in any position within wide portion of slot 14b between proximal end 15 and distal end 16, but cannot inadvertently be removed vertically or longitudinally from wide portion of slot 14b in handle base 10. Handle base 10 also limits rotational movement of thumb slide 30. The total length of longitudinal travel of thumb slide 30 relative to handle base 10 is preferably 5 cm or less. Thumb pad 31 is located between proximal end 82 and distal end 81 of handle base 10. The actuation of thumb pad 31 overlaps the area between proximal end 82 and distal end 81 of handle base 10. A tube or sheath 50 has a proximal end 51, a distal end 52, and may be constructed of polyimide, PTFE, or other flexible material or combination of materials, and has a lumen through its entire length. Sheath 50 has a working length 86 that is preferably between 65 and 125 cm, and the diameter of sheath 50 is preferably approximately 1 mm or less. Sheath 50 passes through opening 12, which is substantially larger in diameter than sheath 50. Proximal end 51 of sheath 50 passes into through hole 32 in thumb slide 30 and is secured to thumb slide 30 using adhesive or other means.

Spinner 20 has a knob portion 24 and a cylindrical portion 23 that has a groove 22 extending around its circumference. Spinner 20 is located at proximal end 82 of handle base 10, with cylindrical portion 23 located within the hollow space of handle base 10 and knob portion 24 of spinner 20 located at proximal end 82 of handle base 10. A hole 21 is located in cylindrical portion 23 along longitudinal axis 11, and extends part way through spinner 20. Knob portion 24 of spinner 20 is axially positioned, and has a diameter 79 that is preferably 1.5 cm or less. Pin 40 has a head 41 and a tip 42. Pin 40 fits snugly into a hole in handle base 10, and tip 42 of pin 40 fits into groove 22. The length of pin 40 is such that when pin 40 is fully seated in the hole with head 41 contacting handle base 10, tip 42 extends into groove 22 in spinner 20, but does not fit snugly in groove 22. Thus spinner 20 is rotatably attached to handle base 10. This configuration limits the longitudinal movement of spinner 20 relative to handle base 10, but permits spinner 20 to rotate freely about longitudinal axis 11 relative to handle base 10.

A drive wire 70 has a proximal end 71 and a distal end 72. An object entrapping assembly or basket 60 is connected to distal end 72. Basket 60 consists of a number of outwardly disposed flexible elements that form a space for entrapping objects. Drive wire 70 may be constructed or formed of stainless steel, nickel titanium alloy, or another metal. Drive wire 70 slidably extends through the lumen of sheath 50, with proximal end 71 of drive wire 70 extending past proximal end 51 of sheath 50. Proximal end 71 of drive wire 70 fits into hole 21 in spinner 20 and is secured using adhesive or other means. Handle assembly 90 has a longitudinally stationary portion that comprises handle base 10, spinner 20, and pin 40.

Figure 3:
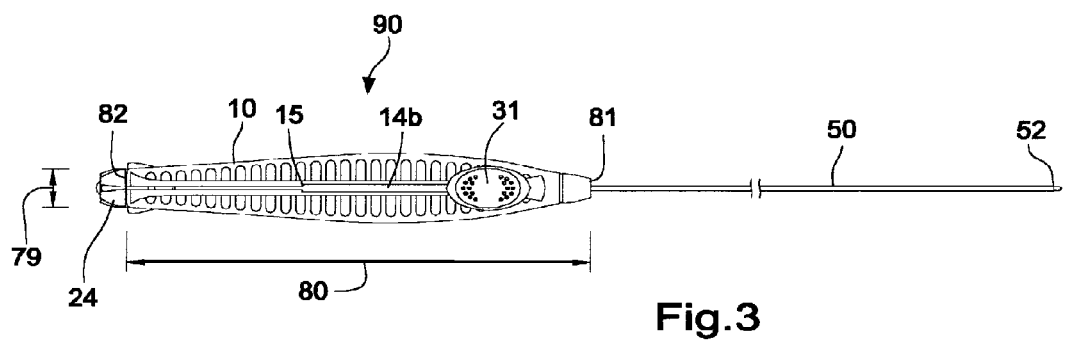
FIG. 3 is a top view of FIG. 1 showing the basket in the retracted, closed, or collapsed position.
Figure 4:
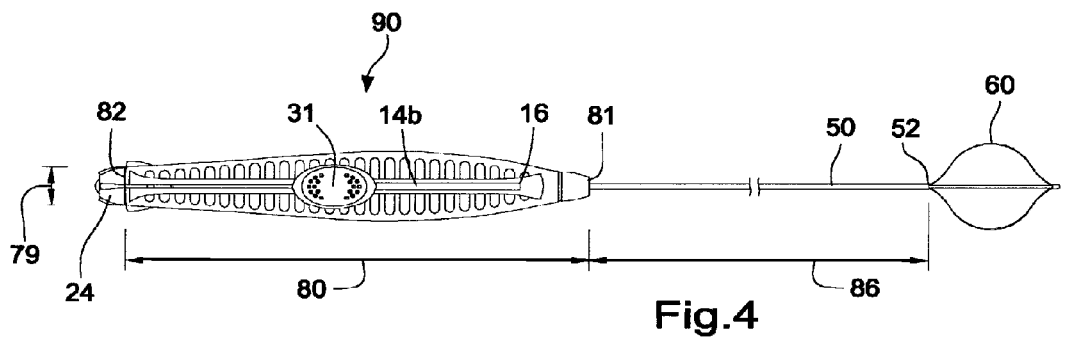
FIG. 4 is a top view of FIG. 1 showing the basket in the extended, open, or expanded position.
Figure 5:
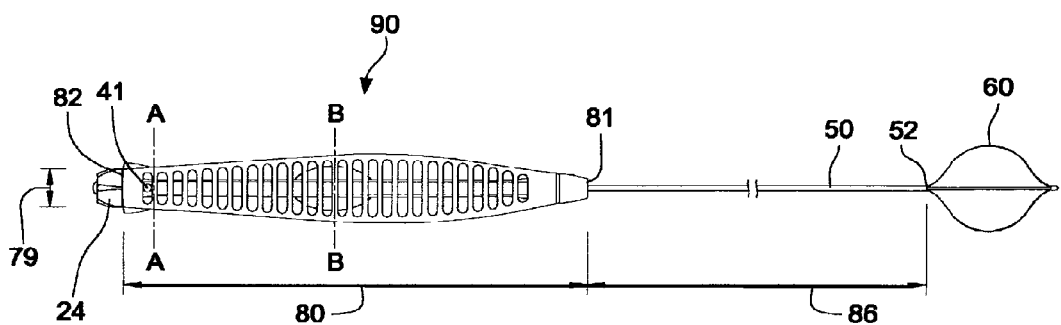
FIG. 5 is a bottom view of FIG. 1 showing the basket in the extended, open, or expanded position.
Figure 5A:
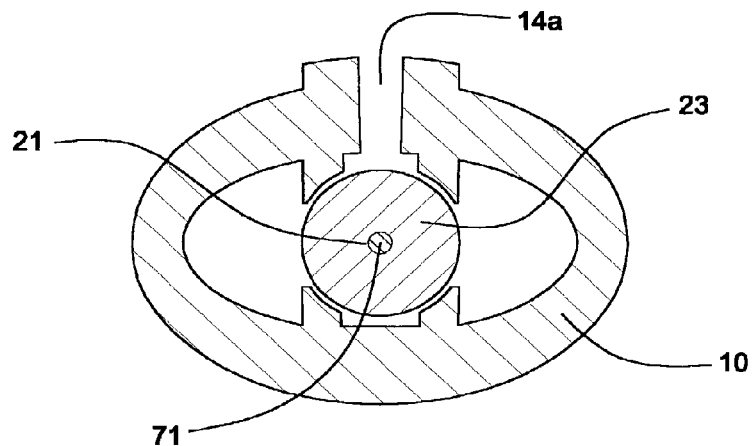
FIG. 5A is a cross sectional view of FIG. 5 taken on line A-A.
Figure 5B:
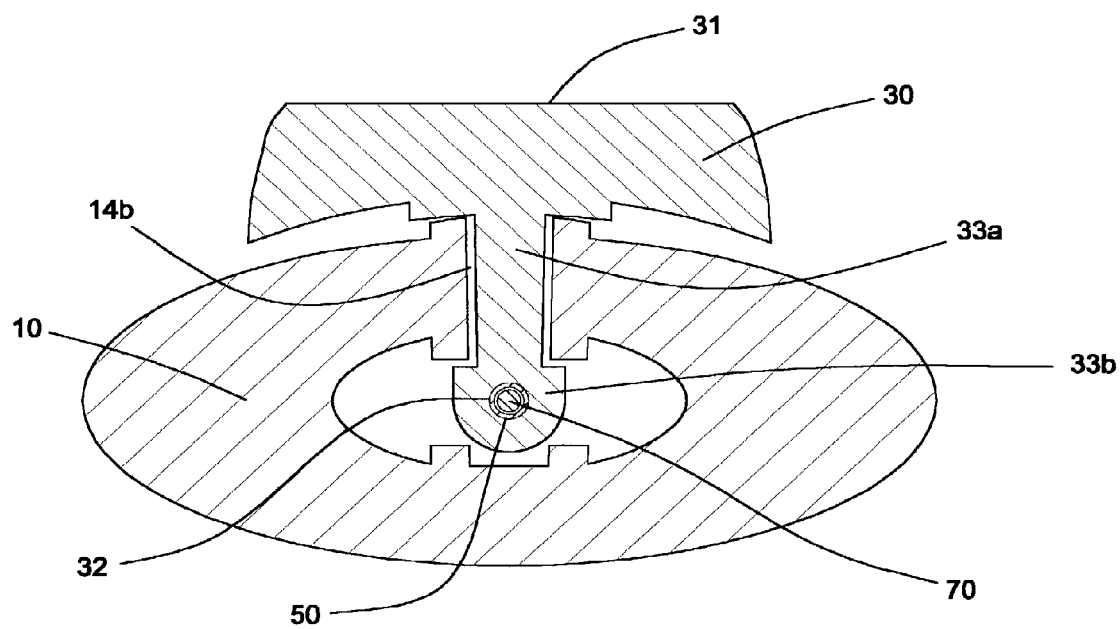
FIG. 5B is a cross sectional view of FIG. 5 taken on line B-B.
Figure 6:
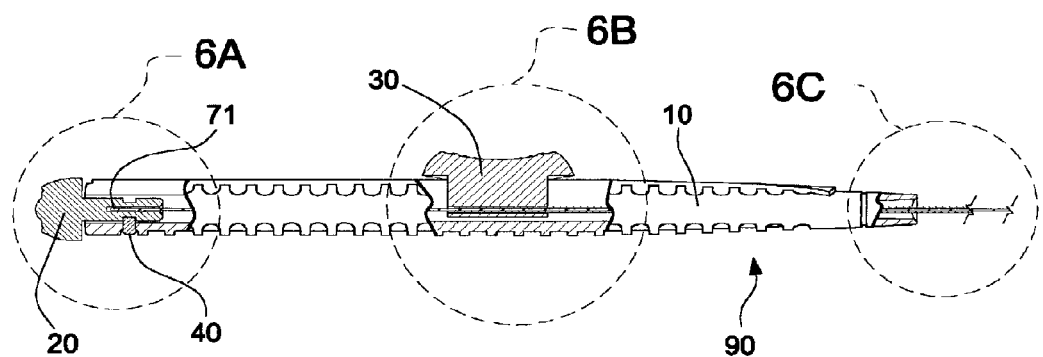
FIG. 6 is a side view, partially in section along the longitudinal axis, of the handle assembly portion of the medical retrieval device in FIG. 1.
Figure 6A:
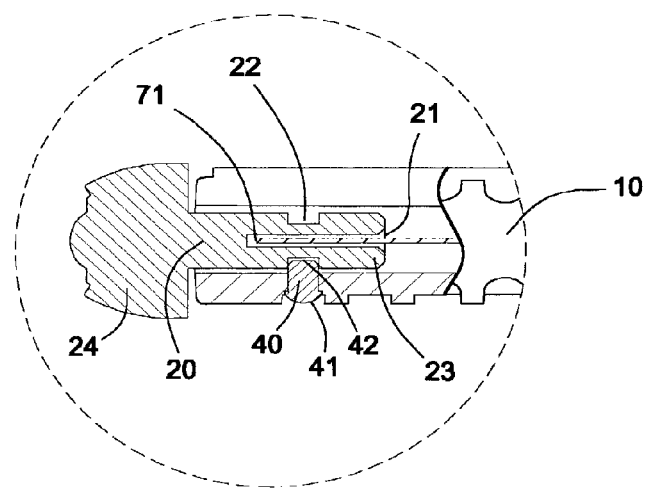
FIG. 6A is an enlarged view of the proximal portion of the handle assembly in FIG. 6.
Figure 6B:
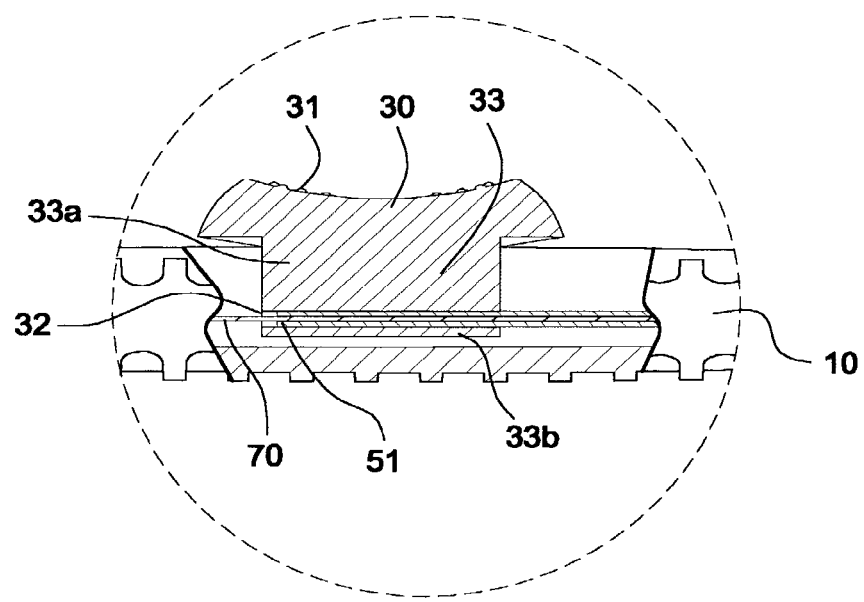
FIG. 6B is an enlarged view of the mid portion of the handle assembly in FIG. 6.
Figure 6C:
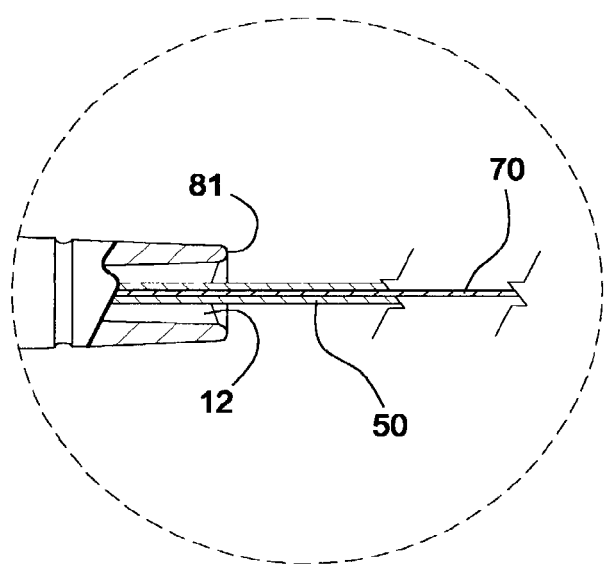
FIG. 6C is an enlarged view of the distal portion of the handle assembly in FIG. 6.
Figure 7:
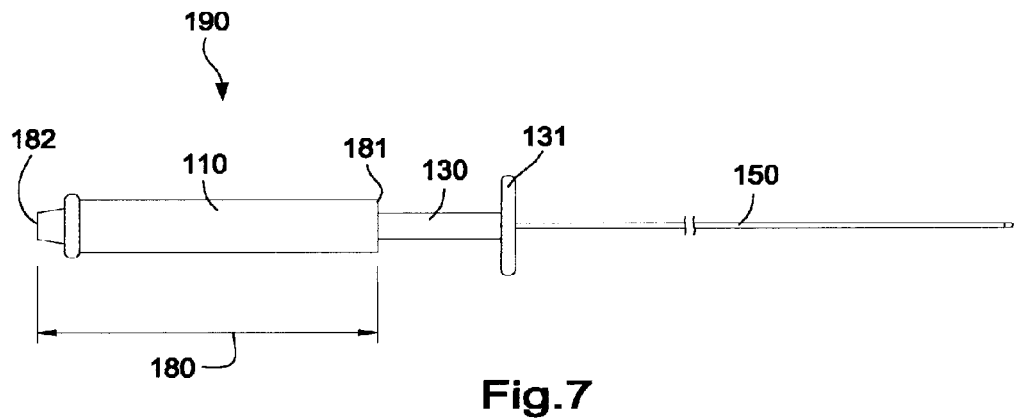
FIG. 7 is side view of a prior art medical retrieval device showing the basket in a retracted position, the top view and bottom view being the same.
Figure 8:
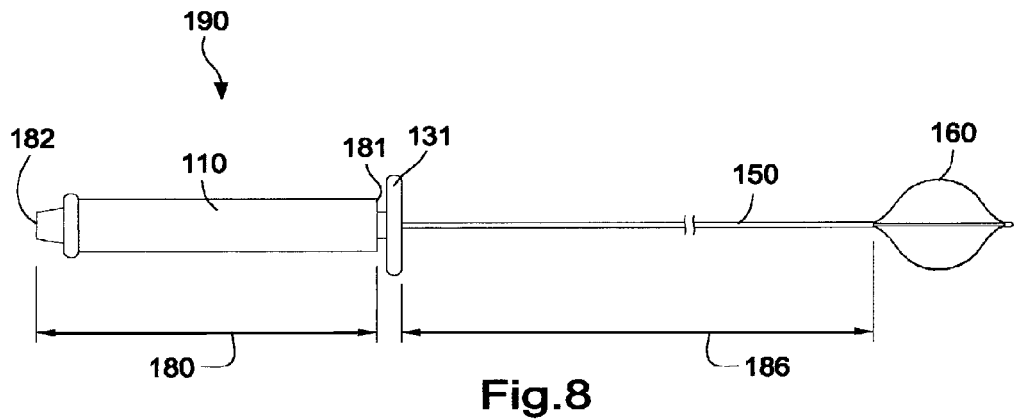
FIG. 8 is a side view of the same prior art device in FIG. 7 but showing the basket in an extended position, the top view and bottom view being the same.

To operate the device, the user wraps four fingers of one hand partially around handle base 10, but not overlapping thumb pad 31. The tip of the thumb of the same hand is placed on thumb pad 31. Referring to FIGS. 1 and 4, basket 60 is in the open or expanded position. In this position, thumb pad 31 is located at proximal end 15 of wide portion of slot 14b. To actuate the device to the closed or refracted position, the user extends the thumb outward from the hand while maintaining contact between the thumb and thumb pad 31 and keeping handle base 10 stationary in the hand. This action causes thumb slide 30 to slide within wide portion of slot 14b toward distal end 16 of wide portion of slot 14b (arrow 55a). This longitudinal movement of thumb slide 30 relative to handle base 10 propels sheath 50 over drive wire 70 (arrow 65b). This enables longitudinal movement of sheath 50 relative to basket 60, forcing basket 60 to collapse and become enclosed within sheath 50. When thumb slide 30 rests at distal end 16 of wide portion of slot 14b, basket 60 is in the completely closed or retracted position within sheath 50, as shown in FIG. 3. If, for example, the object the device is being used to retrieve is a ureteral calculus, the device is introduced in this retracted position through the working channel of an endoscope into the ureter until the retracted basket emerges from the tip of the endoscope in the proximity of the calculus. The user then pulls the thumb back toward the hand, sliding thumb pad 31 back toward proximal end 16 of wide portion of slot 14b (arrow 55a). This action pulls sheath 50 back relative to drive wire 70 and basket 60 (arrow 55b). Basket 60 is then exposed and resumes its expanded shape, as shown in FIGS. 1 and 4.

Handle assembly 90 is then manipulated in order to entrap the object within basket 60. Longitudinal manipulation of basket 60 relative to the object is accomplished by pushing or pulling handle assembly 90 along longitudinal axis 11. Rotational positioning of basket 60 is accomplished by grasping knob 24 of spinner 20 with the thumb and forefinger of the user's second hand, and rotating spinner 20 about longitudinal axis 11 (arrow 65a), relative to handle base 10, which is kept stationary with the first hand. This causes drive wire 70 to rotate within sheath 50, and basket 60 to rotate relative to sheath 50 the same amount in the same direction (arrow 65b). Once the object has been engaged within basket 60, the user then pushes thumb pad 31 forward part way toward distal end 16 of wide portion of slot 14b until basket 60 is partially closed in order to securely hold the object. The device and the endoscope are then simultaneously withdrawn from the patient, holding thumb pad 31 stationary relative to handle base 10 to keep the object secured within basket 60.

It can be seen from the above description that the medical retrieval device according to this invention has a mechanism for precisely rotating the basket that is independent of the extension and retraction actuation mechanism used to collapse and expand the basket. This permits rotation of the basket without requiring the user to rotate the entire handle assembly, allowing for improved user comfort. This also permits rotation of the basket without requiring the sheath to rotate within the working channel of the endoscope, thereby allowing more precise control of basket rotation. The handle base isolates the spinner from the thumb slide actuator. This prevents inadvertent longitudinal actuation of the basket during rotation and inadvertent rotation of the basket during longitudinal actuation. It can also be seen that the handle assembly is of a thumb slide actuated type that is comfortable for the user to hold and operate. It can further be seen that the handle uses a minimal number of parts, reducing cost and simplifying assembly. This gives the desirable result of a handle assembly of a preferred style that allows precise and separate control of the actuation and rotation of the basket, and is comfortable for the user to hold and operate.

Another aspect of the invention is the method of manufacturing the medical retrieval device as described above. More specifically, the method involves steps of injection molding a handle with the above characteristics and assembling the device whereby the device has a rotational means that is independent of and isolated from the actuation means.

Although the description above contains many specificities, these should not be construed as limiting the scope of the invention, but as merely providing illustrations of some of the presently preferred embodiments of this invention. For example, the spinner may be attached to the handle base by different means; a coaxial, dual sheath design may be used; additional and/or alternative materials and joining methods may be used; the handle assembly components may have other configurations or dimensions; other means may be used to control the distance of travel of the thumb slide; the thumb pad may only partially overlap the handle base at part of its travel; a portion of the thumb slide may extend distal to the handle base; the thumb slide and handle base may fit together by different means; the sheath and/or drive wire may be removable from the handle assembly; the basket may have other configurations; the basket may be replaced with another type of tool, such as a grasping assembly or biopsy device; the device may be used without an endoscope; objects other than those mentioned or in different locations in the body may be retrieved, etc.

Thus the scope of the invention should be determined by the appended claims and their legal equivalents, rather than by the examples given.

The invention claimed is:

1. A medical retrieval device for extracting an object comprising:
    a sheath and a drive wire each having a proximal end and a distal end, said drive wire slidably extending through said sheath;
    an object entrapping assembly connected to the distal end of said drive wire for entrapping said object, said object entrapping assembly comprising at least three elements forming a three-dimensional basket for entrapping said object, said sheath for collapsing said object entrapping assembly when retracted into said sheath; and
    a handle assembly located at the proximal ends of said sheath and said drive wire, said handle assembly comprising:
        a base having a proximal end and a distal end defining a fixed longitudinal length and configured to be held in a single hand;
        an actuation mechanism disposed between the proximal end and the distal end of the base, and operably engaged to the sheath, enabling a longitudinal movement of said object entrapping assembly into and out of said sheath; and
        means for rotating the object entrapping assembly for rotational positioning of said object entrapping assembly independent of said longitudinal movement of said actuation mechanism;
    whereby said handle assembly provides for independent rotation and actuation of said object entrapping assembly.

2. The medical retrieval device for extracting an object of claim 1 wherein said means for rotating is located at said proximal end of said base.

3. A medical retrieval device for extracting an object comprising:
    a sheath and a drive wire each having a proximal end and a distal end, said drive wire slidably extending through at least a portion of said sheath;
    an object entrapping assembly connected proximate to the distal end of said drive wire for entrapping said object, said object entrapping assembly having an open configuration and a collapsed configuration; and
    a handle assembly located proximate to the proximal ends of said sheath and said drive wire, said handle assembly comprising:
        a slider directly connected to said sheath,
        a spinner connected directly to said drive wire and unconnected directly to said slider; and
        a base unconnected directly to either of said sheath or said drive wire;
    wherein said spinner can be independently actuated relative to said base, said slider can be independently actuated relative to said base, said spinner can be independently actuated relative to said slider and said slider can be independently actuated relative to said spinner.

* * * * *